United States Patent [19]

Uckun

[11] Patent Number: 4,831,117
[45] Date of Patent: May 16, 1989

[54] MONOCLONAL ANTIBODY SPECIFIC FOR HUMAN B-CELLS

[76] Inventor: Fatih M. Uckun, 330 - 8th St. SE., Minneapolis, Minn. 55414

[21] Appl. No.: 816,141

[22] Filed: Jan. 3, 1986

[51] Int. Cl.$^4$ .................... C12N 5/00; A61K 39/395
[52] U.S. Cl. ............................ 530/387; 435/240.27; 435/68; 435/172.2; 935/104; 935/107; 935/108; 424/85.8; 424/85.91; 530/808
[58] Field of Search ................. 435/240.27, 68, 172.2; 530/387, 808; 935/104, 107, 108, 110; 424/85.8, 85.91

[56] References Cited

PUBLICATIONS

Uckum, F. M. et al. (II) "Increased Efficiency in Selective Elimination of Leukemia Cells by a Combination of a Stable Derivative of Cyclophosphamide and a Human B-Cell-Specific Immunofoxin Containing Pokeweed Antiviral Protein", Cancer Research 45:69-75, Jan. 1985.

Uckun, F. M. et al. (III) "Heterogeneity in Leukemia Cell Populations: A Clear Rationale for Use of Combination Protocols for Ex Vivo Marrow Purging," Transplantation Proceedings, vol. XVII, No. 1, Feb. 1985, pp. 462-464.

Uckun, F. M. et al. (IV) "Immunotoxin-Mediated Elimination of Clonogenic Tumor Cells in the Presence of Human Bone Marrow," J. Immunology, vol. 134, No. 3, Mar. 1985, pp. 2010-2016.

Nadler, L. M. et al. "A Unique Cell Surface Antigen Identifying Lymphoid Malignancies of B Cell Origin," J. Clin. Invest., vol. 67, Jan. 1981, pp. 134-140.

Stashenko, P. et al. "Characterization of a Human B Lymphocyte-Specific Antigen," J. Immunology, vol. 125, No. 4, Oct. 1980, pp. 1678-1685.

Uckun, F. et al. (I) "Selective Elimination of Clonogenic Tumor Cells from Human Bone Marrow by Immunotoxins," Abstract, 1984.

C. S. Abramson et al., J. Immunology, 126, 83 (1981).
L. M. Nadler et al., J. Immunology, 131, 244 (1983).
F. M. Uckun et al., J. Immunology, 134, 2010 (1985).
Copy of ATCC Deposit Contract with respect to hybridoma IST 1586 (ATCC HB 8903), dated Sep. 16, 1985.

Primary Examiner—Margaret Moskowitz
Assistant Examiner—Kay E. Cheney
Attorney, Agent, or Firm—Merchant, Gould, Smith, Edell, Welter & Schmidt

[57] ABSTRACT

A hybrid cell line yields a monoclonal antibody which is highly restricted to B-lineage lymphoblastic leukemia cells and their progenitors.

2 Claims, No Drawings

MONOCLONAL ANTIBODY SPECIFIC FOR HUMAN B-CELLS

BACKGROUND OF THE INVENTION

Autologous bone marrow transplantation (BMT) is currently under evaluation as an alternative approach to allogeneic BMT for the treatment of acute lymphoblastic leukemia (ALL) patients who do not possess matched sibling donors. However, the frequent occurrence of residual leukemia in the remission marrow is a major limitation to the use of autologous BMT. This difficulty makes ex vivo purging of autologous stem cell grafts prior to transplantation essential for therapeutic efficacy. Current ex vivo purging strategies involve the treatment of autologous marrow with cyclophosphamide congeners, monoclonal antibodies (MoAb) plus complement and cytotoxic chemicals bound to MoAb's (immunotoxins). Despite such ex vivo manipulations of autologous stem cell grafts, recurrent leukemia in autotransplanted patients remains the major cause for treatment failure in ALL.

Presently it cannot be determined whether such relapses occur because of incomplete purging of the marrow or incomplete eradication of leukemia in the patients. Present clinical trials usually rely on preclinical studies in which the efficacy of purgative reagents is evaluated against tumor cell lines established in vitro. However, there is a marked heterogeneity in surface antigen expression among leukemia cell populations and neither the phenotype nor the drug or toxin sensitivity of leukemic progenitor cells has been determined. For example, it is believed that none of the monoclonal antibodies or immunotoxins which are currently under clinical evaluation have been tested directly against clonogenic blasts (CFU-L) from ALL patients, and therefore there is no evidence that they can effectively eliminate leukemic progenitor cells.

Therefore a need exists for a monoclonal antibody which is highly specific for ALL progenitor cells while exhibiting no significant binding to pluripotent bone marrow cells. Such a monoclonal antibody could provide the basis for an immunotoxin effective to eliminate leukemic progenitor cells while exhibiting little or no toxicity to normal bone marrow progenitor cells.

SUMMARY OF THE INVENTION

The present invention is directed to a hybridoma cell line, designated IST-1586, and a monoclonal antibody produced thereby, designated B43. Monoclonal antibody B43 is an $IgG_1$ antibody which is highly B-lineage restricted. B43 can detect a B-cell specific antigenic determinant expressed on the earliest known B-cell and which is strongly expressed throughout B-cell differentiation, but not expressed at the terminal stage of differentiation, the plasma cell. For example, the antibody binds to mature B-lymphocytes, pre-B-ALL cells, B-lymphomas, B-lymphoblasts and their leukemic hematopoietic stem cell progenitors, while not significantly cross-reacting with pluripotent stem cells derived from normal bone marrow, T-lymphocytes, granulocytes, platelets, erythrocytes, T-lineage ALL and acute myeloblastic leukemia (AML) cells. Also, those lymphomas which represent the clonal expansion of differentiated malignant B-cells, such as plasma cells of immunocytes (i.e., myeloma and immunocytoma) do not react with B43. The reactivity of cells assayed with B43 which were derived from patients with leukemias or lymphomas is summarized on Table I, below.

TABLE I

| Leukemia/Lymphoma | No. Tested | No. B43-Positive |
| --- | --- | --- |
| Common B-lineage ALL | 54 | 54 |
| T-lineage ALL | 25 | 0 |
| AML[a] | 13 | 0 |
| CLL (B-type)[b] | 3 | 3 |
| CML (B-type)[c] | 3 | 3 |
| B-Lymphoma | 50 | 43 |
| T-Lymphoma | 5 | 0 |
| Histiocytic Lymphoma | 3 | 2 |
| HCL[d] | 2 | 2 |

[a]Acute myelocytic leukemia, [b]Chronic lymphocytic leukemia, [c]Chronic myelocytic leukemia, [d]Histiocytic leukemia Blast crisis To evaluate the clinical potential of B43 MoAb, the antibody was bound to pokeweed antiviral protein (PAP) to provide the B43-PAP immunotoxin. This immunotoxin was tested for its efficacy against leukemic progenitor cells from patients with common B-lineage ALL by evaluating the ability of the IT to eliminate the formation of primary colonies of cultured bone marrow blasts from the patients. Immunotoxin B43-PAP selectively eliminated blast progenitor cells in ten of ten patients while exhibiting minimal toxicity to normal bone marrow progenitor cells. Therefore, monoclonal antibody B43 is useful as the basis for the first monoclonal antibody-based immunotoxin to prove effective against common B-lineage ALL blasts and their progenitors. It is expected that B43-PAP will provide the basis for a highly effective and reproducible procedure to remove residual clonogenic leukemia cells from autologous bone marrow grafts employed in the treatment of common B-lineage acute lymphoblastic leukemia (Common B-ALL), as well as a procedure to treat patients with B-lineage leukemia/lymphoma.

DETAILED DESCRIPTION OF THE INVENTION

Monoclonal Antibodies

The general techniques for producing monoclonal antibodies are based on the fusion of spleen lymphocytes with malignant cells (myelomas) of bone marrow primary tumors [C. Milstein, Sci. Am., 243, 66 (1980)]. The methods yield a hybrid cell line, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen. Moreover, like the myeloma cell lines, the hybrid cell lines are immortal. Specifically, whereas antisera derived from vaccinated animals are variable mixtures of antibodies which cannot be identically reproduced, the single type of immunoglobulin secreted by a hybridoma is specific to one and only one antigenic determinant on the antigen, a complex molecule having a multiplicity of antigenic molecular substructures, or determinants (epitopes). For instance, if the antigen is a protein, an antigenic determinant may be one of the many peptide sequences within the entire protein molecule. Hence, monoclonal antibodies raised against a single antigen may be distinct from each other depending on the determinant that induced their formation. However, all of the antibodies produced by a given clone are identical. Furthermore, preferred hybridoma cell lines can be reproduced indefinitely, are easily propagated in vitro or in vivo, and yield monoclonal antibodies in extremely high concentration.

1. Antigens

Methods for the production of monoclonal antibodies are generally applicable and have been used to produce antibodies to a wide variety of antigens.

Immunogenic antigenic preparations useful to induce the production of anti-ALL antibodies in animals include intact tumor cells bearing several ALL-associated surface determinants, such as Burkitt's lymphoma cells. The number of mammalian B-cells producing antibodies reactive with the immunogen can be increased by additional immunizations ("boosting").

2. Somatic Cells

Somatic cells with the potential for producing antibody, and in particular B cells, are suitable for fusion with a B-cell myeloma line. Those antibody-producing cells undergoing mitosis fuse preferentially. Lymph nodes and spleens of the primed animals are convenient lymphatic organs for use in the present fusion system. Once-primed or hyperimmunized animals can be used as a source of antibody-producing lymphocytes. Mouse and rat lymphocytes give a higher percentage of stable fusions with the mouse myeloma lines described below. However, the use of rabbit, human primate and frog cells is also possible. In the preferred embodiments, hyperimmunized mouse spleen cells are used to make the fused cell hybrids.

3. Myeloma Cells

Specialized myeloma cell lines have been developed from lymphocyte tumors for use in hybridoma-producing fusion procedures [G. Kohler and C. Milstein, Eur. J. Immunol., 6, 511 (1976); M. Shulman et al., Nature, 276, 269 (1978)]. The cell lines have been developed to facilitate the selection of fused hybridomas among unfused and similarly indefinitely self-propagating myeloma cells by using myelomas with enzyme deficiencies that render them incapable of growing in certain selective media that support the growth of hybridomas. Furthermore, myeloma cell lines incapable of producing light or heavy immunoglobulin chains or those deficient in antibody secretion mechanisms are used. A third reason for selection of cell lines is for their suitability and efficiency for fusion.

Several myeloma cell lines may be used for the production of fused cell hybrids, including P3/X63-Ag 8.653, P3/NSI/1-Ag 4-1 ("NS-1"), Sp2/0-Ag14 and S194/5.XXO.BU.1. The P3/X63-Ag 8 and P3/NSI/1-Ag 4-1 cell lines have been described by Kohler and Milstein [Eur. J. Immunol., 6, 511 (1976)]and by J. Kearney et al., J. Immunol., 123, 1548 (1979). Shulman et al. [Nature, 276, 269 (1978) developed the Sp2/0-Ag14 myeloma line. The S194/5.XXO.BU.1 myeloma line was reported in an article by Trowbridge [J. Exp. Med., 148, 313 (1979)].

4. Fusion

Methods for generating hybrids of antibody-producing spleen or lymph node cells and myeloma cells usually comprise mixing somatic cells with myeloma cells in a 3-5:1 proportion (though the proportion may vary from 20:1 to 1:1), respectively, in the presence of an agent or agents that promote the fusion of cell membranes. It is preferred that the same species of animal serve as the source of the somatic and myeloma cells used in the fusion procedure. Fusion methods have been described by Kohler and Milstein in Nature, 256, 495 (1975) and Eur. J. Immunol., 6, 511 (1976), and by Gefter et al. in Somatic Cell Genet, 3, 231 (1977). The fusion-promoting agents used by those investigators were Sendai virus and polyethylene glycol (PEG), respectively. The fusion procedure of the example of the present invention is that of V. Oi et al., as set forth in Selected Methods in Cellular Immunology, W.H. Freeman and Co., San Francisco (1980) at pages 351-372, the disclosure of which is incorporated by reference herein. This method employed PEG as the fusion agent.

5. Isolation of Clones and Antibody Detection and Production

Generally the selection of fused cell hybrids is accomplished by culturing the cells in media that support the growth of hybridomas but prevent the growth of the unfused myeloma cells which normally would go on dividing indefinitely. In the example of the present invention, myeloma cells lacking hypoxanthine phosphoribosyl transferase (HPRT−) were used. These cells are selected against in hypoxanthine/aminopterin/thymidine (HAT) medium, a medium in which the fused cell hybrids survive due to the HPRT-positive phenotype of the spleen cells. The use of myeloma cells with different genetic deficiencies (e.g., other enzyme deficiencies, drug sensitivities, and the like) that can be selected against in media supporting the growth of genotypically competent hybrids is also possible.

Several weeks can be required to selectively culture the fused cell hybrids. Early in this time period, it is necessary to identify those hybrids which produce the desired antibody so that they may be subsequently cloned and propagated. The detection of antibody-producing hybrids can be achieved by any one of several standard assay methods, including indirect immunofluorescence, enzyme-linked immunoassay and radioimmunoassay techniques which have been described in the literature [R. Kennet, T. McKearn and K. Bechtol (editors), Monoclonal Antibodies, Hybridomas: A New Dimension In Biological Analyses, Plenum Press, New York (1980) at pages 376-384 ].

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops a malignant ascites or bulky tumors secreting the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium, also containing high concentrations of a single specific monoclonal antibody, can be harvested by decantation, filtration or centrifugation, and the antibody isolated therefrom.

6. Isotyping of Monoclonal Antibodies

Immunoglobulin isotype and subclass can be determined by the Ouchterlony immunoprecipitation technique using goat or rabbit anti-mouse immunoglobulin subclass antibodies, or by indirect immunofluorescence using isotope specific anti-mouse antisera.

7. Characterization of Monoclonal Antibodies and Immuntoxins (a) Specificity Testing The binding reactivity of B43 and of the other monoclonal antibodies employed in the present invention can be evaluated by the indirect immunofluorescence assay. In this assay, the cells to be tested are contacted in a suspension or on a slide with an excess of the MoAb. After a suitable incubation period, the cells were washed to free them of unbound MoAb and the bound antibody detected with an anti-mouse antibody bound to a fluorescent label such as fluorescein isothiocyanate (FITC).

The binding of the B43-PAP immunotoxin (B43-PAP IT) to leukemic blasts can be determined by a "double sandwich" type immunofluorescence assay wherein the cells to be assayed are incubated sequentially with (a) the immunotoxin, (b) an antiserum to the pokeweed antiviral protein, and (c) a fluorescent-labelled antibody to the antiserum. The labelled cells can be analyzed by cytofluorometric technics using appropriate background subtraction techniques.

(b) Evaluation of Immunotoxin Cytotoxicity

Cells such as bone marrow blasts obtained from aspirated bone marrow samples can be contacted with the B43-PAP immunotoxin by suspending the cells in a suitable physiological medium and adding the IT to the desired concentration. Following B43-PAP treatment, the survival of the leukemic progenitor cells can be measured by suspending the blasts in alpha-MEM supplemented with phytohemagglutinin-stimulated lymphocyte conditioned medium (PHA-LCM). Samples of the blast suspension are then cultured for a week and viable colonies, if any, detected by microscopy.

The invention will be further described by reference to the following detailed examples.

I. Preparation of Monoclonal Antibody B43

A. Immunization

Two 8-10-week-old female BALB/c mice were immunized i.p. with Burkitt's lymphoma cells (2x10$^7$ lymphoma cells in 1 ml serum-free phosphate buffered saline solution [PBS]). Tumor cells were obtained from an abdominal lymph node specimen removed by surgery from an 18-year-old male patient with Burkitt's lymphoma (stage D, ileocecal tumor mass, abdominal lymph nodes and bone marrow were involved). Three weeks later, the primary immunization was followed by boosting with cryopreserved lymphoma cells from the same patient both i.v. and i.p. on 3 subsequent days (Days 1-3)(0.5×10$^7$ lymphoma cells/0.5 ml PBS i.v. and 0.5×10$^7$ lymphoma cells/0.5 ml PBS i.p.). Fusion was performed on Day 4.

B. Somatic Cell Hybridization, Selection, Growth and Initial Characterization of Hybridomas On Day 4, the mouse spleens were removed aseptically and a mononuclear spleen cell suspension was prepared by first breaking up spleens on a wire mesh, suspending with a pipet, settling out the clumps of debris and applying density gradient separation (Ficoll-Hypaque, 1.077g/cm$^3$). Splenocytes were fused with X63-Ag 8.653 mouse myeloma cells by conventional somatic cell hybridization techniques.

Splenocytes and myeloma cells were mixed together in a total volume of 1 ml of serum-free minimal essential medium (DMEM) in a splenocyte:myeloma cell ratio of 4:1. One ml of warm (37° C) polyethylene glycol solution (l0g PEG 4000 10 ml distilled H$_2$O +1 ml DMSO) was dropwise added over a period of one minute shaking at 37° C. to the cell suspension. After a 90-second period of shaking at 37° C., the cell suspension was gradually diluted with serum-free DMEM (total end volume=50 ml) and left at 20° C. for 5 min. Subsequently, cells were washed twice in serum-free DMEM (00° C., 400g, 10 min.) and resuspended in RPMI 1640 medium +20% (v/v) FCS. The cell concentration was adjusted to 2×10$^6$ cells/ml and a 100 ul volume of the cell suspension was placed into replicate wells (2×10$^5$ cell/well) of 96-well flat-bottom tissue culture plates. Each well contained a monoplayer of BALB/c peritoneal macrophages (5×10$^3$ macrophages in 100 $\mu$l RPMI 1640 +20% (v/v) FCS per well) as feeders.

On Days 7 and 14 after fusion, 100 $\mu$l of the supernatant was removed from each well and replaced by 100 $\mu$l of freshly prepared HAT-medium. After the appearance of hybrid colonies at Days 15-20, 100 $\mu$l portions of supernatant from each of the wells showing growth were harvested and tested for the presence of antibodies reactive with the Burkitt's lymphoma cells used for immunization by indirect immunofluorescence using a Zeiss-fluorescent microscope. Hybridoma cells from antibody-positive wells were harvested and subcultured at 10$^3$, 10$^2$ and 10$^1$ cells/well in RPMI 1640 +20% (v/v) FCS on a monolayer of BALB/c peritoneal macrophages. Subcultures were incubated at 37° C./5% CO$_2$ in a humidified atmosphere for 7 days.

Subsequently, supernatants were assayed for the presence of antibodies as described above. Hybridoma cells from 10 of the subcultures with the highest titer of Burkitt's lymphoma reactive antibody were subcultured by limiting dilution in the absence of feeder cells. Subcloning was performed two additional times from antibody-positive wells started initially with <0.3 hybridoma cells/well. Subsequently, antibody secreting clones were expanded, transferred to tissue culture flasks and the supernatants were used for further characterization of the antibodies by indirect immunofluorescence using different target cells.

The supernatant of subclone IST-1586 appeared to be B-lineage restricted in its reactivity and did not cross-react with the T-lymphocytes, granulocytes, platelets, erythrocytes, T-ALL and AML cells used for screening.

Using FITC-goat anti-mouse antibodies and Ouchterlony immunoprecipitation techniques, the isotype of the antibody secreted by this hybrid cell line, designated B43, was determined to be IgG$_1$.

Hybridoma cells were passaged at least three times into pristane-primed mice to produce ascites fluids containing high titers of B43 monoclonal antibody. Female BALB/c mice were primed with 0.5 ml i.p. pristane 2 weeks prior to injection of 1 × 10$^6$ passaged hybridoma cells in 1 ml of PBS. Approximately 2-4 weeks after injection, mice developed a hemorrhagic ascites which contained 2-10 mg/ml B43 antibody.

II. Characterization of Monoclonal Antibody B43

The reactivity of B43 with nineteen cell types was assayed and compared with a panel of monoclonal antibodies previously developed to B-cell antigens. The binding (+ = >30% of cells reactive), absence thereof (− = <20% of cells reactive) or intermediate result (+/− = 20-30% of cells reactive) was determined by indirect immunofluorescence. The results of this study are summarized on Table II.

TABLE II
Immunological Profiles of Different Cell Types

| Cells (Line) | Monoclonal Antibody | | | | | |
|---|---|---|---|---|---|---|
| | B43 | B4[a] | BA-1[b] | BA-2[c] | BA-3[d] | B2[e] |
| Pre B-ALL (NALM 6) | + | + | + | + | + | − |
| B-ALL (RAJI) | + | + | − | − | + | + |
| T-ALL (HSB-2) | − | − | − | N/A* | N/A | − |
| AML (HL60) | − | − | − | − | − | − |
| Erythroleukemia (K562) | + | − | + | + | − | − |
| B-lymphocytes | + | + | + | + | − | + |
| Plasma Cells | − | − | − | − | − | − |
| T-lymphocytes | − | − | − | +/− | − | − |
| T Cell Clones | − | − | − | +/− | − | − |
| Monocytes | − | − | − | +/− | − | − |
| Granulocytes | − | − | + | + | + | − |
| Platelets | − | − | − | + | + | − |
| Erythrocytes | − | − | − | − | − | − |
| CFU-GEMM[1] | − | N/A | − | +/− | − | ? |
| BFU-E[2] | − | N/A | − | − | − | ? |
| CFU-E[3] | − | N/A | − | − | − | ? |
| CFU-MK[4] | − | N/A | − | + | ? | ? |
| CFU-GM[5] | − | N/A | − | + | − | ? |
| Stem Cell-DEXTER | − | | | N/A | | |

[1] Pluripotent stem cells from normal bone marrow;
[2] Burst-forming units (erythroid);
[3] Colony-forming units (erythroid);
[4] Colony-forming units (megakaryocyte)
[5] Colony-forming units (granulocyte macrophage);
*No data available.
[a] L. M. Nadler et al., J. Immunology, 131, 244 (1983).
[b] C. S. Abramson et al., J. Immunology, 126, 83 (1981).
[c] I. Royston et al., J. Immunology, 125, 725 (1980).
[d] T. W. LeBien et al., J. Immunology, 129, 2287 (1982).
[e] L. M. Nadler et al., J. Immunology, 126, 1941 (1981).

B43 MoAb was found to react with substantially all of the B lymphocytes isolated from peripheral blood and lymphoid organs, as well as with six B-ALL and six pre-B-ALL cell lines. Cells from the majority of patients with B cell lymphoma, CML (blast crisis, B-type), CLL (B-type), common B-lineage ALL and HCL also express the antigenic determinant recognized by B43 MoAb. In contrast, patients with AML, T-cell ALL or T-cell derived non-Hodgkin's lymphoma show no reactivity with B43. MoAb B43 does not bind to normal monopotent bone marrow progenitor cells, e.g., committed myelomonocytic (CFU-GM), erythroid (CFU-E), or megakaryocytoid (CFU-MK) precursors. Granulocytes, erythrocytes, platelets, T-lymphocytes and plasma cells are also not bound by B43.

Although the reactivity exhibited by the B4 MoAb is superficially similar to that exhibited by the B43 MoAb, the B4 antigen has been characterized as a glycoprotein of native molecular weight of about 120,000, while the antigen recognized by the B43 monoclonal antibody is a proteolipid.

The presence of free binding sites can be best and most accurately examined by using immunotoxins, since binding of a small number of immunotoxin molecules is followed by internalization and results in irreversible cell death. Therefore, to determine the ability of the B4 and B43 MoAb's to block the binding of the B43-PAP IT, RAJI (B-ALL) cells were preincubated with 10 ug/ml B4 MoAb or 10 ug/ml B43 MoAb. Subsequently, B43-PAP IT ($4 \times 10^{-8}$M) was added to the cell suspension. Binding of the B43-PAP IT was evaluated using anti-PAP antibodies and the "double sandwich" type immunofluorescence assay as described in section 7(a) hereinabove. Controls were sham-treated before addition of the immunotoxin. The cytotoxicity was assayed by determining the inhibition of protein synthesis in the target cells [F. M. Uckun et al., J. Immunology, 134, 2010 (1985)]and by the clonogenic assay described in section IV (B) hereinbelow. It was determined that (1) B43, but not B4, blocks the subsequent binding of the B43-PAP IT, and (2) B43, but not B4, blocks B43-PAP-mediated cytotoxicity to B43-positive RAJI cells. These results provide further evidence that the cell surface determinants defined by the B43 and B4 MoAb's are essentially different.

Furthermore, the B43 MoAb does not bind to non-hematopoetic tissues, i.e., lung, kidney, brain, liver, endothelium, muscle and skin. This is the only B-lineage restricted MoAb known with such strict specificity.

III. Immunotoxin Synthesis

Pokeweed antiviral protein (PAP) is a single chain polypeptide toxin (m.w. 29,000) that catalytically inactivates the 60S subunit of eukaryotic ribosomes and can be isolated from the spring leaves of pokeweed (*Phytolacca americana*) as described by L. L. Houston et al., in J. Biol. Chem., 25, 9601 (1983).

Monoclonal antibodies B43 (IgG1, pan-B), 3A1 (IgG1, pan-T, anti-IgM CD7) [A. Bernard et al., Leukocyte Typing: Human leukocyte differentiation antigens detected by monoclonal antibodies, Springer-Verlag, Berlin (1984) at page 25]and T101 (IgG$_2$a, pan-T, anti-CD5) [I. Royston et al., J. Immunol., 125, 725 (1980)]were linked to pokeweed antiviral protein (PAP) by a disulfide bond using N-succinimidyl-3-(2-pyridyldithio)propionate (SPDP) as described by S. Ramakrishnan et al., in Cancer Research, 44, 201 (1984). Pan-T immunotoxins (IT) were purified on a Sephacryl S-200 column ($1 \times 150$cm).

Pan-B B43-PAP IT was purified by adsorbtion on protein A sepharose as described by F. M. Uckun et al., in J. Immunology, 134, 2010 (1985). No free PAP was detected on polyacrylamide gel electrophoresis under non-reducing conditions. Free antibody contamination was estimated to be less than 20% by gel electrophoresis. The molar ratio of PAP to IgG in the conjugates was estimated by a specific homologous radioimmunoassay using radioiodinated PAP as described by S. Ramakrishnan et al., in Biochim Biophys. Acta, 719, 341 (1982). By competitive inhibition of 125I-PAP binding to rabbit anti-PAP antibodies by PAP and PAP containing IT, this ratio was found to be 2:1 in B43-PAP, 1:1 in 3A1-PAP and 1:1 in T1.1 -PAP.

IT were evaluated for their ability to inactivate protein synthesis in a cell-free translation system in which rat liver ribosomes and a polyuridylic acid were employed by the method of D. B. Cawley et al., Biochemistry, 17, 2648 (1979). All three IT were found to be equally potent inhibitors of polyuridylic acid translation at equimolar concentrations (data not shown). An average molecular weight of 180,000 (3A1-PAP, T101-PAP) or 210,000 (B43-PAP) was assigned to the immunotoxins to calculate the molar concentrations established hereinbelow.

IV. Immunotoxin Inhibition of ALL Progenitor Cells

A. Patient Material

Twelve patients with ALL were included in this study. Clinical and diagnostic data are summarized in Table III

TABLE III
CLINICAL AND DIAGNOSTIC DATA ON PATIENTS WITH ACUTE LYMPHOBLASTIC LEUKEMIA (ALL)

| Patient No. | Sex | Age (Yr.) | Diagnosis (FAB) | New Case or Relapse | Bone Marrow Percent Blasts |
|---|---|---|---|---|---|
| 1 | M | 18 | L1 | New | 97 |
| 2 | M | 3 | L2 | New | 99 |
| 3 | F | 5 | L1 | Relapse | 94 |
| 4 | M | 9 | L1 | Relapse | 91 |
| 5 | F | 1 | L1 | New | 91 |
| 6 | F | 12 | L1 | Relapse | 91 |
| 7 | M | 2 | L1 | Relapse | 100 |
| 8 | F | 2 | L1 | New | 100 |
| 9 | F | 2 | L2 | New | 79 |
| 10 | F | 2 | L1 | New | 100 |
| 11 | F | 4 | L1 | New | 100 |
| 12 | M | 5 | L1 | New | 95 |

Bone marrow aspirate samples were procured by conventional methods. Morphological classification was performed on Wright-Giemsa stained slides using a modification of the original FAB classification as described by D. Miller et al., Brit. J. Hematology, 48, 199 (1981). Blast cells were isolated by a single density gradient centrifugation on Ficoll-Hypaque (1.077g/cm$^3$). Marker analyses by indirect immunofluorescence and flow cytometry were performed using a panel of MoAb which define B-lineage (i.e., B43, BA-1, BA-2, BA-3) and T-lineage (i.e., 35.1, T101, 3A-1) associated leukocyte differentiation antigens. FITC-labelled goat F(ab')$_2$ anti-mouse IgG (Cappel Laboratories, Cochranville, NC) served as secondary antibody. Surface immunoglobulin (sIg) was assayed by direct immunofluorescence using FITC-conjugated goat F(ab')$_2$ antihuman total immunoglobulins IgG (Kallestad, Austin, TX). Background fluorescence was determined by incubating cells with an IgG$_{2a}$ murine myeloma protein (UPC 10, Litton Biogenetics, Charleston, SC). Cells were analyzed for immunofluorescence using a Spectrum III Cytofluorograph (Ortho Diagnostics, Raritan, NJ). Attempts were made to examine only the lymphoblasts within each specimen by appropriate gating. Samples were scored as positive when >20% of the cells bound the antibody used.

B. Colony Assay for Common B-Lineage ALL Progenitor Cells

Freshly obtained bone marrow blasts were suspended in alpha-MEM supplemented with 0.9% methylcellulose, 15% FCS, 15% platelet rich fresh human plasma, 10% PHA-LCM, 1% MEM vitamin solution, 0.5% MEM amino acids solution, 0.5% MEM non-essential amino acid solution, 2mM L-glutamine, 1 mM sodium pyruvate, 50 µM 2-mercaptoethanol, 4 µg/ml DL-serine and 4 µg/ml asparagine.

PHA-LCM was prepared by culturing 1×10$^7$ peripheral blood mononuclear cells per ml from a patient with polycythemia vera for 4 days at 37° C./5% CO$_2$ in alpha MEM containing 1% (v/v) PHA (HA15, Wellcome Reagents) and 1% human albumin (Sigma 10GM). All batches of PHA-LCM, fetal calf serum and human plasma were titrated to determine the optimal concentrations and kept frozen at −20° C. until use.

Duplicate 1 ml samples of the suspension were cultured in 35 mm Petri dishes for 7 days at 37° C. in a humidified, 5% CO$_2$ atmosphere. On Day 7, colonies containing more than 20 cells were counted using an inverted phase microscope with high optical resolution. Subsequently, all colonies were pooled for further cytochemical and immunological analysis of colony blasts. As described hereinbelow, cultures were started with 10$^5$ bone marrow mononuclear cells (BMMNC)/ml. In some experiments, 10$^4$ cells from pooled colonies were replated under the initial culture conditions to measure the self-renewal ability of blast progenitors.

C. Cytochemical and Immunological Analysis of Colony Blasts

Cells from pooled colonies were deposited on slides by cytocentrifugation. The morphology of lymphoblasts was studied in Wright-Giemsa stained cytospin preparations. In cytochemical studies, lymphoblasts were evaluated for staining by periodic-acid Schiff (PAS) by the McManus method and for non-specific esterase (NSE) activity using alphanaphtyl acetate as substrate [R. W. McKenna et al., Am. J. Ped. Heme-Onc., 3, 263 (1979)]. Sudan Black B and myeloperoxidase stains were also used to detect contaminating normal myelomonocytic cells.

For surface marker analyses by indirect immunofluorescence, slides were fixed in acetone (10 min.), dried and 100 µl MoAb was added directly on top of cells. Monoclonal antibodies were used in antibody excess. After 30 min. of incubation at room temperature in a humidity chamber, cells were washed twice in PBS to remove unbound antibody. FITC-conjugated goat F(ab')$_2$ anti-mouse IgG (Cappel Laboratories, Cochranville, N.C.) was used as second antibody (incubation for 30 min., then washed 3× in PBS). For background fluorescence in IgG$_{2a}$ murine myeloma protein (UPC 10, Litton Biogenetics, Charleston, SC) was substituted for the MoAb. The percentage of cells expressing each marker was determined using a Zeiss fluorescent microscope equipped with Ploem epi-illumination. Quantitative data were obtained from examination of 100–200 cells. The marker profiles were analyzed using a panel of murine MoAb which define lymphoid and myeloid-/ervthroid (ME) differentiation antigens. Specifically, we used the following MoAb's:

T-cell panel: (1) 35.1 (anti-CD2[T,p50])[P. J. Martin et al., J. Immunol., 131, 180 (1983)], (2) T101 (antiCD5[T,p67][I. Royston et al., J. Immunol., 125, 725 (1980)], (3) 3A1 (anti-CD7[T,p41][A. Bernard et al., ibid.].

B-cell panel:. (1) BA-2 (anti-CD9[nT-nB,p24], (2) BA-3 (anti-CD10[nT-nB,p100], (3) B43 (pan-B), 4) BA-1 (anti-CD24[B,G,p45,55,65].

ME-panel: (1) anti-MY8 [J. D. Griffin et al., op. cit., Leukocyte Typing at page 404), (2) RIO (anti-glycophorin A)[M. F. Greaves et al., Blood, 61, 645 (1983)].

Serological cluster designations were assigned as at the First (Paris, 1982) and Second (Boston, 1984) International Workshops on Human Leukocyte Differentiation Antigens.

D. Immunotoxin Binding

The binding of B43-PAP IT to leukemic blasts was determined by a "double sandwich" method in which the cells were incubated in a sequential fashion with (1) IT (4×10$^{-8}$M, 30 min., 40° C.), (2) affinity purified rabbit anti-Pap anti-serum (50 ug/ml, 15 min., 4° C.) and 3) FITC-conjugated goat anti-rabbit IgG (Miles Laboratories, Elkhart, IN)(1:50 dilution, 15 min., 4° C) as described by F. M. Uckun et al., J. Immunology, 134, 2010 (1985). Cells were analyzed by cytofluorometry using a FACS IV (Becton Dickinson, Mountain View, CA). Fluorescence profiles were plotted with the aid of an Apple II computer as histograms of relative intensity over 256 channels versus number of cells in each channel. Background fluorescence staining was obtained by incubating cells with an equimolar mixture of free MoAb (B43, 3A1, T101, 4x10-8M each) and unconjugated PAP ($8 \times 10^{-8}$M) in place of PAP-IT.

E. Treatment of Cells with Immunotoxins

Ten million cells/ml were treated with IT for 8 hr (standard protocol) or 4 hr (short incubation protocol) at 37° C./5% $CO_2$ in RPMI 1640 +20% (v/v) FCS. After treatment cells were washed twice in RPMI 1640 +5% (v/v) FCS to remove unbound IT.

F. Evaluation of the Cytotoxicity of B43-PAP against Common B-Lineage ALL Progenitor Cells Following B43-PAP treatment, the survival of leukemic progenitor cells was measured using the colony assay described herein above. The extent of cytotoxicity was expressed as percent inhibition of leukemic progenitor cells and was calculated using the formula:

$$\text{Percent Inhibition of Blast Progenitors} = 100 - \frac{\text{Mean No. of Blast Colonies}/10^5 \text{ treated cells}}{\text{Mean No. of Colonies}/10^5 \text{ untreated cells}} \times 100$$

These experiments employed the following controls: 1) untreated samples, (2) samples treated with two control IT directed against T-lineage associated surface determinants (i.e., 3A1-PAP and T101-PAP) and (3) samples treated with a mixture of free B43 MoAb and unconjugated PAP. The non-specific cytotoxicity of B43-PAP IT against normal bone marrow progenitor cells was evaluated in stem cell colony assays.

G. Stem Cell Colony Assays

Toxicity of B43-PAP IT treatment (8 hr, 37° C.) against normal monopotent (CFU-GE, CFU-E, CFU-MK) and pluripotent (CFU-GEMM) bone marrow progenitor cells was evaluated by colony assays. The detailed methodology of this colony assay system has been described by F. M. Uckun et al., Cancer Research, 45, 69 (1985). Data were expressed as percent control colony formation using the formula:

$$\text{Percent Control Colony Formation} = \frac{\text{Mean No. of Colonies}/10^5 \text{ treated cells}}{\text{Mean No. of Colonies}/10^5 \text{ untreated cells}} \times 100$$

H. Immunological Marker Profiles of Common B-Lineage ALL Cells

Twelve patients with ALL were studied. The immunological profiles of the patients'bone marrow mononuclear cells (BMMNC) are shown in Table IV.

TABLE IV

IMMUNOLOGICAL MARKER PROFILES OF PATIENTS' BONE MARROW BLASTS

| Patient No. | T-Lineage Markers* | | | B-Lineage Markers* | | | | |
|---|---|---|---|---|---|---|---|---|
| | CD2 35.1 | CD5 T101 | CD7 3AI | CD9 BA-2 | CD10 BA-3 | B43 | CD24 BA-1 | sIg+ |
| 1 | 4 | 4 | 3 | 92 | 59 | 87 | 88 | 4 |
| 2 | 13 | 9 | 5 | 83 | 94 | 77 | 88 | 11 |
| 3 | 5 | 4 | 3 | 85 | 79 | 87 | 42 | 3 |
| 4 | 1 | 1 | 0 | 72 | 87 | 91 | 95 | 1 |
| 5 | 3 | 3 | 3 | 75 | 33 | 76 | 91 | 7 |
| 6 | 7 | 3 | 3 | 94 | 94 | 83 | 95 | 5 |
| 7 | 1 | 1 | 1 | 96 | 61 | 94 | 90 | 3 |
| 8 | 2 | 2 | 2 | 90 | 73 | 87 | 41 | 5 |
| 9 | 11 | 12 | 10 | 75 | 78 | 74 | 85 | 14 |
| 10 | 5 | 4 | 4 | 72 | 95 | 85 | 96 | 2 |
| 11 | 2 | 2 | | 34 | 98 | 79 | 98 | 4 |
| 12 | 8 | 5 | 0 | 39 | 82 | 83 | 86 | 7 |

*Numbers represent percentage of cells reactive with the given antibodies directed against T- and B-lineage surface determinants.
+sIg: surface immunoglobulin The marrow blasts from all the patients expressed the B-lineage restricted surface determinant recognized by the B43 MoAb. No patient expressed the T-lineage associated markers CD2(T,p50), CD5(T,p67) or CD7(T,p41). The cells from all the patients also reacted with BA-3, a MoAb directed against CD10 (nT-nB,p100)/CALLA surface determinant. There was a marked variability in the number of BA-3 positive bone marrow blasts among the patient population ranging from 33% (patient #5) to 98% (patient #11)(median, 80.5%). All patients expressed the B-lineage associated antigens CD9 and CD24 but lacked significant sIg.

I. Binding of B43-PAP Immunotoxin to Common B-Lineage ALL Cells

Bone marrow blasts from patients were examined for the presence of bound immunotoxin (IT) after treatment with $4 \times 10^{-8}$M PAP IT. Common B-lineage ALL cells reacted with the B43-PAP immunotoxin in 12 of 12 cases studied. The number of B43-PAP labelled cells ranged from 77.1% (patient #5) to 96.0% (patient #7)(median, 86.3%). By contrast, these blasts did not bind control IT 3A1-PAP and T101-PAP which are directed against T-lineage associated surface determinants.

J. Colony Forming and Self-renewing Abilities of Common B-Lineage ALL Progenitor Cells Freshly obtained bone marrow blasts from 12 common B-lineage ALL patients were assayed for primary colony formation in vitro. Successful cultures were obtained in 10 of 12 cases. Paired daughter cells appeared in 8 of these 10 cases within 24 hr. In 2 cases (i.e., patient #2 and patient #4) there was a lag period of approximately 48 hr until the first paired blasts were observed. After 72 hr of incubation, spherical clusters of 10-20 tightly associated cells were discernible in all successful cultures (i.e., 10 of 12 cases). Colonies containing more than 20 blasts were counted on Day 7. The blasts in these colonies were round and had a translucent cytoplasm with a distinct cell border of high refractility. Colonies were compact and usually contained less than 200 cells. More than 2000 distinct colonies could be accurately counted in a single 35mm Petri dish.

Blast colony formation was linear with respect to numbers of cultured cells at between $1 \times 10^3$ and $1 \times 10^5$ leukemic blasts per Petri dish. The apparent cloning frequency of blast progenitor cells in cultures started with $1 \times 10^5$ leukemic blasts veried from 0.09% (i.e., 90 colonies/$10^5$ BM blasts) to 2.63% (i.e., 2630 colonies/$10^5$ BM blasts). In the 10 cases with successful cultures, Day 7 blast colonies displayed a marked variability in cell number ranging from approximately 20 cells to more than 200 cells per colony.

K. Morphological, Cytochemical and Immunological Characteristics of Cultured Blasts The cells from pooled colonies showed >95% viability as estimated by trypan blue exclusion. They had blast morphology with a basophilic cytoplasm, prominent vacuo-exclusion, irregular nuclear membrane and prominent nucleoli. The colony blasts from different patients displayed marked differences with respect to (1) size, (2) nuclear/cytoplasmic ratio, (3) basophilia of cytoplasm, (4) nuclear membrane contour, (5) size, number and prominence of nucleoli and (6) amount and prominence of vacuolation. Cytochemical evaluation of colony blasts showed that they are Sudan-black negative, myeloperoxidase negative, non-specific esterase negative and periodic acid-Schiff (PAS) positive. The PAS positive cells showed a strong staining intensity. The stain was irregularly distributed within the cytoplasm and occurred in clumps or coarse and fine granules. In summary, colony cells had morphologic and cytochemical features consistent with ALL.

As indicated by the data summarized on Table V, blasts from pooled Day 7 colonies displayed a marked heterogeneity in expression of B-lineage associated surface determinants.

CD10/CALLA in this group (Table V). The second major group was comprised of 3 cases (p't Nos. 1, 5 and 11) in which the cells in the blast colonies did not express CD10/CALLA. In this group, the expression of CD24 was also significantly greater on the uncultured initial blast population than on the cells pooled from Day 7 blast colonies (Table V). In the remaining 3 cases (p't Nos. 3, 4 and 10) cultured blasts had marker profiles which differed from the evaluation prior to culture as well as from the immunological phenotype observed in the 2 major groups described above. It should be noted that there was no apparent correlation between the expression of B-lineage associated antigens on cultured blasts and the number or size of blast colonies.

In 10 of 10 cases with successful cultures, the colony blasts did not express T-lineage associated antigens (i.e., CD2, CD5 and CD7) or myeloid/erythroid markers (i.e., MY8 and glycophorin A) but were stained with at least 2 different MoAb's directed against distinct B-line-

TABLE V

IMMUNOLOGICAL MARKER PROFILES OF CULTURED CELLS POOLED FROM DAY 7 BLAST COLONIES

| Patient No. | T-Lineage Markers* | | | B-Lineage Markers* | | | | Myeloid/Erythroid Markers | |
|---|---|---|---|---|---|---|---|---|---|
| | CD2 35.1 | CD5 T101 | CD7 3A1 | CD9 BA-2 | CD10 BA-3 | B43 | CD24 BA-1 | Anti-MY 8 | Anti-glycophorin A (R10) |
| 1 | 1 | 2 | 0 | 97 | 0 | 98 | 25 | 2 | 0 |
| 2 | 0 | NT | NT | 95 | 67 | 94 | 92 | 0 | NT |
| 3 | 2 | 0 | 0 | 90 | 40 | 90 | 35 | 1 | NT |
| 4 | 1 | NT | NT | 65 | 84 | 55 | 34 | 0 | NT |
| 5 | 0 | NT | NT | 85 | 0 | 66 | 40 | 0 | NT |
| 6 | 0 | NT | NT | 98 | 78 | 95 | 93 | 0 | 0 |
| 7 | 0 | 0 | 2 | 99 | 58 | 85 | 91 | 3 | 1 |
| 8 | 0 | NT | NT | 86 | 66 | 75 | 90 | NT | NT |
| 9 | no colony formation | | | no colony formation | | | | no colony formation | |
| 10 | 1 | 0 | 0 | 49 | 27 | 74 | 85 | 1 | 0 |
| 11 | 0 | NT | 0 | 95 | 0 | 90 | 10 | 0 | 0 |
| 12 | no colony formation | | | no colony formation | | | | no colony formation | |

*Surface marker analyses by indirect immunofluorescence were performed on acetone fixed cytospin preparations. The number of cells expressing each marker was determined using a Zeiss fluorescent microscope. Quantitative data were obtained from examination of 100–200 cells. Numbers represent percentage of colony blasts reactive with the MoAb.
NT = not tested.

In 3 of 10 cases (patient Nos. 2, 6 and 7) the immunological phenotype of colony blasts was identical to that of the bulk blast population before culture and in the remaining 7 cases it differed from the pre-culture evaluation.

Two major immunological groups could be identified based on the reactivity pattern with BA-2 (anti-CD9), BA-3 (anti-CD10), BA-1 (anti-CD24) and B43 monoclonal antibodies. The first group included of 4 cases (p't Nos. 2, 6, 7 and 8). Colony blasts in this group had BA-2+, BA-3+, BA-1+, B43+marker profiles. Thus, their immunological phenotype was consistent with that of bone marrow lymphoblasts before culture. In particular, 58–78% of cultured blasts expressed age associated surface determinants. Despite considerable heterogeneity, the marker profiles detailed in Table V are consistent with B-lineage ALL. In all cases a large fraction of cultured blasts in Day 7 colonies expressed the B-lineage associated surface determinant defined by B43 MoAb.

L. B43-PAP Induced Inhibition of Common B-Lineage ALL Progenitor Cells

The immunotherapeutic potential of B43-PAP was evaluated in a clonogenic assay system. Table VI shows the efficacy of B43-PAP against leukemic bone marrow progenitor cells from common B-lineage ALL patients.

TABLE VI

EFFECT OF IMMUNOTOXIN TREATMENT ON COMMON B-LINEAGE ALL PROGENITOR CELLS*

| | Mean No. of Blast Colonies/$10^5$ BMMNC | | | | | | Percent Inhibition of Blast Progenitor Cells | | | | |
|---|---|---|---|---|---|---|---|---|---|---|---|
| Patient No. | No Treatment | B43-MoAb +PAP (8 hr) | B43-PAP (8 hr) | B43-PAP (4 hr) | 3A1-PAP (8 hr) | T101-PAP (8 hr) | B43-MoAb +PAP (8 hr) | B43-PAP (8 hr) | B43-PAP (4 hr) | 3A1-PAP (8 hr) | T101-PAP (8 hr) |
| 1 | 1850 | 1925 | 0 | 0 | 1710 | NT+ | 0.00 | ≧99.95 | ≧99.95 | 7.57 | NT |
| 2 | 160 | 155 | 0 | 0 | 210 | NT | 3.13 | ≧99.38 | ≧99.38 | 0.00 | NT |
| 3 | 1150 | 983 | 0 | 0 | 1001 | NT | 14.52 | ≧99.91 | ≧99.91 | 12.96 | NT |
| 4 | 90 | 132 | 0 | NT | 103 | 95 | 0.00 | ≧98.89 | NT | 0.00 | 0.00 |
| 5 | 210 | 205 | 2.5 | NT | 253 | 213 | 2.38 | 98.81 | NT | 0.00 | 0.00 |
| 6 | 197 | 163 | 0 | NT | NT | 208 | 17.26 | ≧99.49 | NT | NT | 0.00 |
| 7 | 2631 | 2540 | 0 | NT | 2701 | 2230 | 3.46 | ≧99.96 | NT | 0.00 | 15.24 |
| 8 | 113 | 125 | 9 | NT | NT | 102 | 0.00 | 92.00 | NT | NT | 9.73 |
| 9 | | | no colony growth | | | | | | no colony growth | | |

TABLE VI-continued

| | EFFECT OF IMMUNOTOXIN TREATMENT ON COMMON B-LINEAGE ALL PROGENITOR CELLS* | | | | | | | | | |
|---|---|---|---|---|---|---|---|---|---|---|
| | Mean No. of Blast Colonies/$10^5$ BMMNC | | | | | Percent Inhibition of Blast Progenitor Cells | | | | |
| Patient No. | No Treatment | B43-MoAb +PAP (8 hr) | B43-PAP (8 hr) | B43-PAP (4 hr) | 3A1-PAP (8 hr) | T101-PAP (8 hr) | B43-MoAb +PAP (8 hr) | B43-PAP (8 hr) | B43-PAP (4 hr) | 3A1-PAP (8 hr) | T101-PAP (8 hr) |
| 10 | 514 | 502 | NT | 0 | NT | 487 | 2.33 | NT | ≧99.81 | NT | 5.25 |
| 11 | 505 | 643 | NT | 0 | NT | 525 | 0.00 | NT | ≧99.80 | NT | 0.00 |
| 12 | no colony growth | | | | | | no colony growth | | | | |

*Following IT treatment (4 × $10^{-8}$ M) at 37° C. for the indicated time periods, the survival of leukemic B-lineage progenitor cells was measured in the colony assay system.
+NT: not tested.

No blast colonies were detected in 6 of 8 leukemic bone marrow samples treated with 4×$10^{-8}$M B43-PAP for 8 hr at 37° C. Four hours incubation with B43-PAP proved as effective as 8 hr incubation and no residual blast colonies were detected in immunotoxin treated samples from any of 5 patients tested (Table VI). In summary, colony formation was completely inhibited in 8 of 10 cases by B43-PAP (4 hr or 8 hr incubations at 37° C.). The inhibition of leukemic progenitor cells ranged from 92% (patient #8) to >99.96% (p't #7) with a mean value of ≧98.9%.

In contrast to the toxicity of B43-PAP, a mixture of 4×$10^{-8}$M free B43 MoAb and 8×$10^{-8}$M unconjugated PAP did not elicit a significant inhibition of blast progenitor cells. Control IT 3A1-PAP and T101-PAP only minimally affected the colony forming ability of common B-lineage ALL progenitor cells (Table VI).

M. Effect of B43-PAP on Normal Monopotent (CFU-GM, CFU-E, CFU-MK) and Pluripotent (CFU-GEMM) Bone Marrow Progenitor Cells Bone marrow mononuclear cells (BMMNC) from 2 healthy individuals were examined for B43-PAP reactivity by indirect immunofluorescence and flow cytometry. The percentage of B43-PAP labelled BMMNC was 9.1% and 8.1%, respectively. Control cultures yielded 159 (range:150-170) granulocyte-macrophage (GM-), 118 (range:105-131) erythroid (E-), 12.8 (range:-8-20) pure megakaryocyte (MK-) and 19 (range: 16-21) multilineage (GEMM-) colonies per $10^5$ HMMNC. At $10^{-8}$ M B43-PAP monopotent and pluripotent progenitors were only minimally affected. At 4×$10^{-8}$M, 33% of CFU-GM, 48.5% of CFU-E and 35.5% of CFU-GEMM were inhibited. Megakaryocyte progenitors (CFU-MK) were inhibited only 4%. As shown in Table VI, B43-PAP eliminated up to 99.96% of common B-lineage ALL progenitor cells at this immunotoxin concentration.

V. Discussion

A novel colony assay system has been employed to evaluate the cytotoxicity of B43-PAP, a human B cell directed immunotoxin, against sIg-negative B-lineage leukemic bone marrow progenitor cells freshly obtained from ALL patients. A maximum kill of ≧99.96% of leukemic progenitor cells was achieved after treatment with B43-PAP under conditions in which less than 40% of normal pluripotent hematopoietic progenitor cells (CFU-GEMM) were inhibited. B43-PAP completely inhibited primary blast colony formation in 8 of 10 common B-lineage ALL cases. These data establish that the B-lineage associated surface determinant recognized by B43-MoAb is expressed on common B-lineage ALL progenitor cells in sufficient quantities to allow effective binding and internalization of the immunotoxin. Our findings further illustrate that B-lineage blast progenitors are sensitive to pokeweed antiviral protein at the ribosomal level. Thus, it is expected that immunotoxins containing the B43 MoAb bound to pokeweed antiviral protein will be useful for in vivo elimination of residual leukemic progenitor cells from patients with common B-lineage ALL, as well as for ex vivo purging of autologous marrow grafts in these patients prior to autologous bone marrow transplantation.

Monoclonal antibody B43 is secreted by hybrid cell line IST-1586 which has been deposited with the American Type Culture Collection, 12301 Parklawn Drive Rockville, MD, U.S.A. and has been assigned accession number ATCC HB 8903.

A culture of the deposited microorganism will be made available to the public upon the grant of patent based upon the present application. It is to be understood that the availability of a deposit does not constitute a license to practice the subject invention in derogation of patent rights granted by the United States government. Furthermore, the present invention is not to be limited in scope by the microorganism deposited, since the deposited embodiment is intended as a single illustration of one aspect of the invention. Indeed, various modifications of the invention in addition to those shown and described herein will become apparent to those skilled in the art from the foregoing description.

For example, other hybridomas and the monoclonal antibodies secreted thereby which exhibit the novel properties of IST-1586 and B43 are intended to fall within the scope of the present invention. Such antibodies include those capable of substantially blocking the binding of the B43 antibody to its receptor site on human B-cells. Likewise, such hybridomas include other immortal cell lines capable of secreting MoAb's capable of blocking the binding of the B43 MoAb to its B-cell receptor site. Other such modifications are intended to fall within the scope of the appended claims.

What is claimed is:

1. A hybridoma which secretes a B-lineage restricted monoclonal antibody of isotype IgG, having all the identifying characteristics of hybrid cell line ATCC HB 8903.

2. The monoclonal antibody produced by hybrid cell line ATCC HB 8903.

* * * * *

UNITED STATES PATENT AND TRADEMARK OFFICE
CERTIFICATE OF CORRECTION

PATENT NO. : 4,831,117

DATED : May 16, 1989

INVENTOR(S) : Fatih M. Uckun

It is certified that error appears in the above-identified patent and that said Letters Patent is hereby corrected as shown below:

Column 3, line 52
"(1976)]and" should be -- (1976)] and --

Column 5, line 38
"(2x107" should be --(2 x $10^7$--

Column 5, line 65
after "4000" insert -- + --

Column 6, line 4
"(00°" should be --(20° --

Column 8, line 1
"(1985)]and" should be -- (1985)] and --

Column 8, line 23
"(IgG1," (both) should be -- ($IgG_1$ --

Column 8, line 27
"25]and" should be --25] and --

Column 8, line 28
"(1980]were" should be --(1980] were --

Column 8, line 46
"125I-PAP" should be -- $^{125}I$-PAP --

UNITED STATES PATENT AND TRADEMARK OFFICE
CERTIFICATE OF CORRECTION

PATENT NO. : 4,831,117

DATED : May 16, 1989

INVENTOR(S) : Fatih M. Uckun

It is certified that error appears in the above-identified patent and that said Letters Patent is hereby corrected as shown below:

Column 8, line 49
"T1.1-PAP" should be -- T101-PAP. --

Column 8, line 68
after "III" insert a period

Column 10, line 36
"/eruthroid" should be --/erythroid --

Column 10, line 40
after "ti" insert a hyphen

Column 11, line 2
"4x10-8M" should be -- $4 \times 10^{-8} M$ --

Column 11, line 7
"CO2" should be --$CO_2$--

Column 11, line 34
"CFU - GE" should be -- CFU-GM --

Column 12, line 58
"veried" should be -- varied --

UNITED STATES PATENT AND TRADEMARK OFFICE
CERTIFICATE OF CORRECTION

PATENT NO. : 4,831,117

DATED : May 16, 1989

INVENTOR(S) : Fatih M. Uckun

It is certified that error appears in the above-identified patent and that said Letters Patent is hereby corrected as shown below:

Column 15, line 22
  ">99.96%" should be -- $\geq$99.96% --

Column 15, line 41
  "HMMNC" should be -- BMMNC --

Column 16, line 28
  after "drive" insert a comma

Signed and Sealed this

Twentieth Day of February, 1990

*Attest:*

JEFFREY M. SAMUELS

*Attesting Officer*  *Acting Commissioner of Patents and Trademarks*